(12) United States Patent
Fletcher

(10) Patent No.: US 6,511,502 B2
(45) Date of Patent: Jan. 28, 2003

(54) APPARATUS FOR AND METHOD OF COOLING A BRAIN

(76) Inventor: Robert David Fletcher, 120 Duke, Apt. 801, Hamilton, Ontario (CA), L8P 4T1

( * ) Notice: Subject to any disclaimer, the term of this patent is extended or adjusted under 35 U.S.C. 154(b) by 81 days.

(21) Appl. No.: 09/793,553

(22) Filed: Feb. 27, 2001

(65) Prior Publication Data

US 2002/0120317 A1 Aug. 29, 2002

(51) Int. Cl.[7] .................................................. A61F 7/00
(52) U.S. Cl. ........................................ 607/109; 607/104
(58) Field of Search ............................... 607/104, 109, 607/114, 108, 96

(56) References Cited

U.S. PATENT DOCUMENTS

| 3,674,034 A | * | 7/1972 | Hardy | 607/104 |
|---|---|---|---|---|
| 4,566,455 A | | 1/1986 | Kramer | 128/380 |
| 4,750,493 A | | 6/1988 | Brader | 128/380 |
| 4,783,866 A | | 11/1988 | Simmons | 5/441 |
| 4,920,963 A | | 5/1990 | Brader | 128/402 |
| 4,962,761 A | * | 10/1990 | Golden | 607/104 |
| 5,072,875 A | * | 12/1991 | Zacoi | 607/104 |
| 5,190,032 A | | 3/1993 | Zacol | 128/400 |
| 5,292,347 A | * | 3/1994 | Pompei | 607/104 |
| 5,486,204 A | | 1/1996 | Clifton | 607/96 |
| 5,643,336 A | | 7/1997 | Lopez-Claros | 607/104 |
| 5,897,581 A | | 4/1999 | Fronda | 607/109 |
| 5,913,885 A | * | 6/1999 | Klatz et al. | 607/104 |
| 5,916,242 A | * | 6/1999 | Schwartz | 607/113 |
| 5,957,964 A | | 9/1999 | Ceravolo | 607/109 |
| 6,030,412 A | | 2/2000 | Klatz | 607/104 |
| 6,197,045 B1 | * | 3/2001 | Carson | 607/112 |
| 6,416,532 B1 | * | 7/2002 | Fallik | 607/109 |

* cited by examiner

*Primary Examiner*—Linda C. M. Dvorak
*Assistant Examiner*—Jocelyn Ram
(74) *Attorney, Agent, or Firm*—I. Zborovsky

(57) ABSTRACT

Cooling a patient's brain is performed by each of two hollow pads exclusively in an area of a patient's neck adjoining one of carotid arteries by circulating a cooling liquid through one of the pads independently from the other pad or through both pads, to cool either one half of the brain, or another half of the brain, or both halves thereof.

6 Claims, 2 Drawing Sheets

APPARATUS FOR AND METHOD OF COOLING A BRAIN

BACKGROUND OF THE INVENTION

The present invention relates to a method of cooling a brain.

For many years it has been known that deep hypothermia (less than 32° C.) can improve survival from ischemic brain injuries. The practicalities of these treatments preclude its use in acute stroke. The patient has to be paralyzed and placed on a ventilator for 48 hours for the treatment effect to be seen. Recently, some articles were published that indicated benefits to the ischemic brain of modest hypothermia (35° C.) which is two degrees below normal body temperature. In both studies the practicality issue is apparent by use of cooling blankets on the patients. This requires the patient to remain bedridden and/or paralyzed and on the ventilator to obtain the apparent positive outcome. The complications of bedridden patients are well known (i.e. pulmonary embolus, pressure sores, and pneumonia). Several solutions for cooling body parts have been suggested in U.S. Pat. Nos. 5,916,242; 4,566,455; 4,750,493; 4,763,866; 4,020,963; 5,190,032; 5,486,204; 5,643,336; 5,897,581; 5,913,855; 5,057,964; 6,030,412. Some of these patents deal with cooling of a patient's brain which can be performed by various apparatuses, for example by a circular collar applied over the whole periphery of the neck. The existing apparatuses can be further improved.

SUMMARY OF THE INVENTION

Accordingly, it is an object of the present invention to provide a method of cooling a brain, which avoids the disadvantages of the prior art.

In keeping with these objects and with others which will become apparent hereinafter, one feature of present invention resides, briefly stated, in a method of cooling of a brain which includes the steps of applying each of two hollow pads exclusively to an area of a patient's neck adjoining one of carotid arteries so that when applied said hollow pads contact the areas exclusively adjacent to the carotid arteries and are spaced from one another; and supplying by liquid circulating means a cooling liquid from a liquid source to a respective one of said pads and withdrawing the liquid from the same pad, whereby the cooling liquid can circulate either through one of said pads independently from the other of said pads, or the cooling liquid can circulate through the other of said pads independently from one of said pads, or both said pads, to cool either one half of the brain, or another half of the brain, or both halves thereof.

When the method is performed in accordance with the present invention, it becomes possible for the first time to selectively cool either a left part of the brain or a right part of the brain, or both parts simultaneously. This is important because in some instances it is necessary to cool only one half of the brain when this half of the brain is damaged. Also, the remaining part of the neck between the areas of the carotid arteries are not cooled, since cooling of this remaining part is undesirable especially in view of increased sensitivity of the back of the neck. When it is exactly determined which part of the brain is damaged by a stroke, then a corresponding one of the pads which is applied on the area of the carotid artery leading to the damaged part of the brain in cooled, and cooled blood flows to the damages part of the brain. In emergency situations it is possible to activate the cooling liquid circulation through both pads before a determination is made which part of the brain is damaged, to make sure that hypothermia is immediately administered. Thereafter, when it is determined which part of the brain is damaged, the cooling is concentrated exclusively on the carotid artery leading to the damaged part of the brain.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
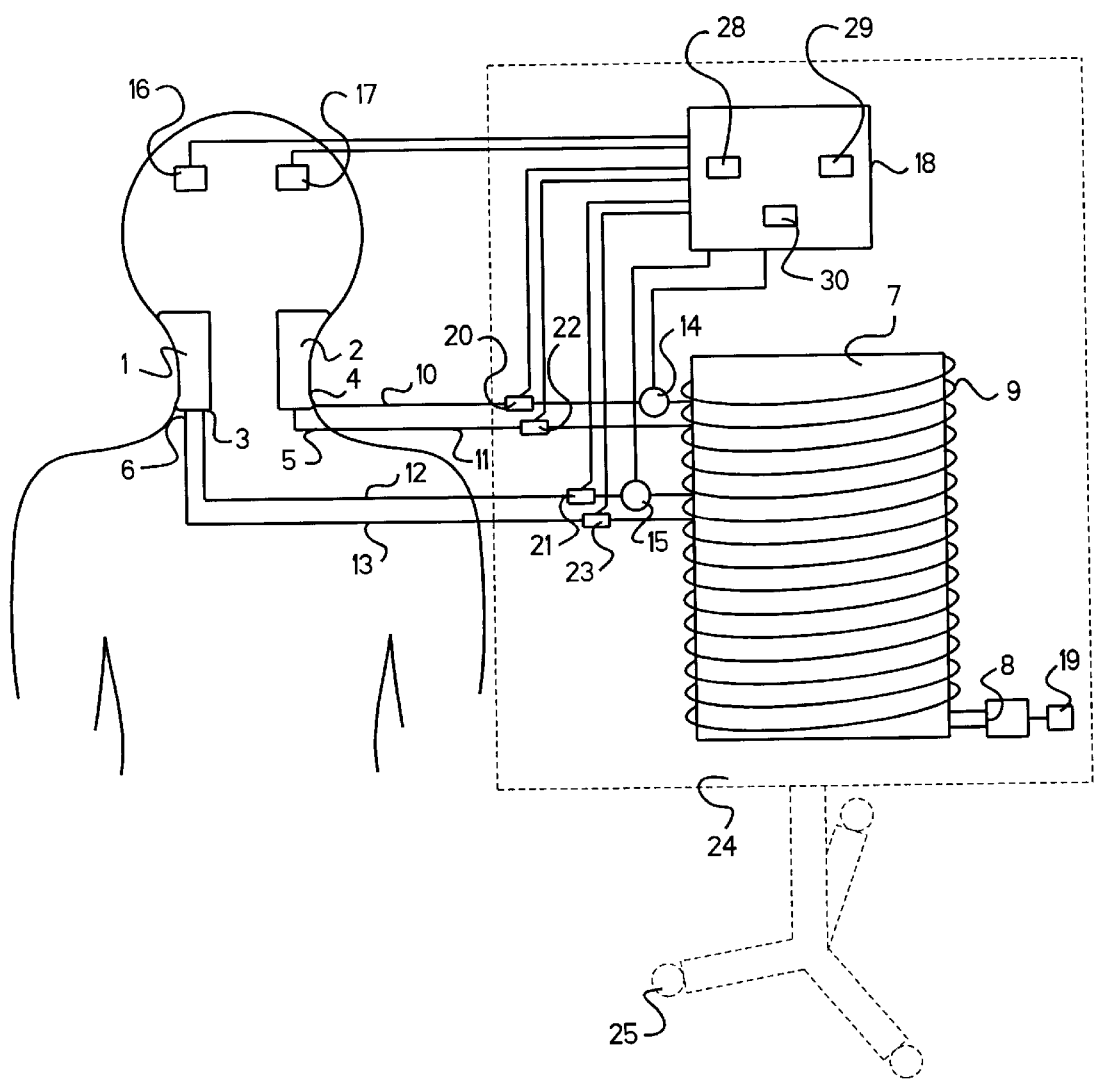
FIG. 1 is a view schematically showing an apparatus for cooling the brain, which performs the inventive method.

An apparatus for performing a method in accordance with the present invention includes two hollow pads which are identified with reference numerals 1 and 2. The dimensions of the hollow pads 1 or 2 are selected so that each of the hollow pads can be applied exclusively on an area of a corresponding carotid artery leading to a brain. In other words, each pad covers the immediate narrowing strip on the neck which extends along the carotid artery and small areas around this narrow strip. The pads 1 and 2 have inlets 3 and 4 for supplying a cooling liquid into the pads and outlet 5 and 6 for withdrawing the liquid from the pads. The preferable liquid for cooling the brain is water, since it does not cause frost bite.

The apparatus further has a source of cooling liquids which is identified with reference numeral 7. The cooling liquid source 7 can be formed as a liquid reservoir provided with corresponding inlets, outlets, faucets, etc., which are not shown in the drawings in detail for the sake clarity. Means for cooling the cooling liquid reservoir 7 are further provided. They can include a compressor 8 which supplies a refrigerant into a cooling coil 9 which surrounds the reservoir 7.

Cooling liquid circulating means are further provided for circulating the cooling liquid through each of the pads 1 and 2, independently from one another. The first cooling circulating means include a supply line 10 which leads from the cooling liquid reservoir 7 to the inlet 4 of the pad 2 so as to supply the cooling liquid into the pad 2, and a return conduit which connects the outlet 5 to the pad 2 with the cooling reservoir 7 to withdraw the liquid from the pad 2 back into the cooling liquid reservoir 7. The second circulating means include a supply conduit 12 which connects the cooling liquid reservoir 7 with the inlet 3 of the pad 1 for supplying the cooling liquid into the pad 1, and a return conduit 13 which connects the outlet 6 of the pad 1 with the cooling liquid reservoir 7 to withdraw the liquid from the pad 1 back into the reservoir. Pumps 14 and 15 are provided for pumping the cooling liquid from the reservoir 7 into the supply line 12 and then withdrawing the liquid through the return lines 11 and 13 back to the reservoir 7. The pumps 14 and 15 can be arranged outside or inside the liquid reservoir 7. The pumps are formed as adjustable pumps. They can adjust a speed of liquid supply, a flow rate of the liquid supply, etc.

The apparatus further has means for monitoring cooling process of the patient's brain. The monitoring means includes sensors for monitoring the temperature of each half of the brain. The sensors are identified with reference numerals 16 and 17. They are attachable to a corresponding part of the patient's head and connected to a monitoring and control unit 18. The monitoring and control unit is connected with a device which adjusts the temperature of the cooling liquid, for example a thermostat 19. The thermostat 19 is connected with the pump 18 and can control the supply of the refrigerant so as to adjust the cooling temperature of the liquid in the reservoir 7, depending on the temperature of a corresponding half of the brain sensed by the sensors 16, 17.

The monitoring means further includes liquid temperature sensors 20 and 21 arranged in the supply lines 10 and 12 which supply the liquid from the reservoir 7 to the pads 1 and 2. Also, additional sensors 22, 23 can be provided on the return lines 11 and 13. The sensors 20–23 sense the temperature of the liquid in two separate liquid circulating means and supply corresponding signals to the monitoring and control unit 18, in which signals these temperatures are processed and used for controlling for example of the thermostat 19 for correspondingly cooling the liquid supply from the cooling reservoir 7.

The basic units of the apparatus, in particular the cooling liquid reservoir 7, the compressor 8, the monitoring and control unit 18, the pumps 14, 15, the sensors 20–23 are mounted on a support 24 which can be placed on wheels 25. Therefore, a patient can obtain the treatment, in particular cooling of the brain, and at the same time can be mobile and not bedridden. The patient can walk over corresponding distances with the apparatus moving beside said patient on the wheels.

The lines 10, 11, 12, 13 can be formed as transparent hoses. They can be connected to the inlets and outlets 3–6 by releasable connections, for example in the form of plug-in elements so that they can be easily connected to and disconnected from the pads.

Figure 2:
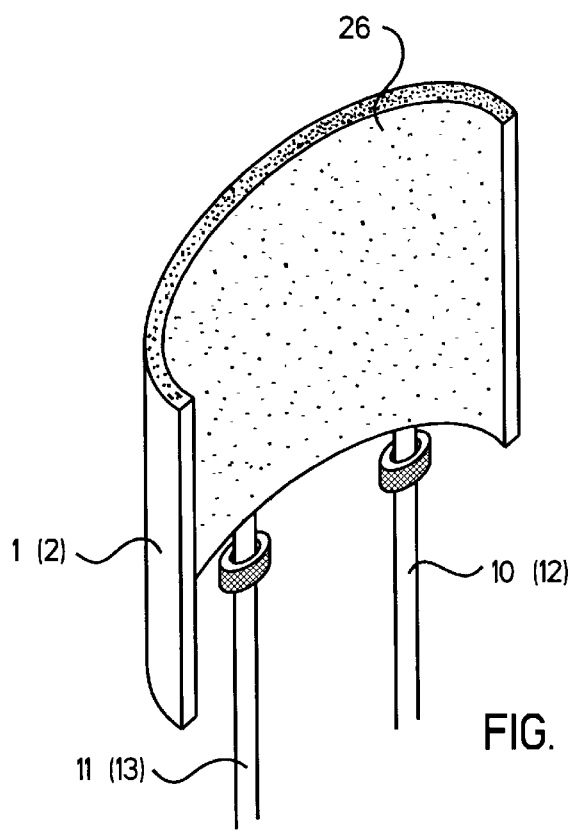
FIG. 2 is a view schematically showing one of the cooling pads of the inventive apparatus.
Figure 3:
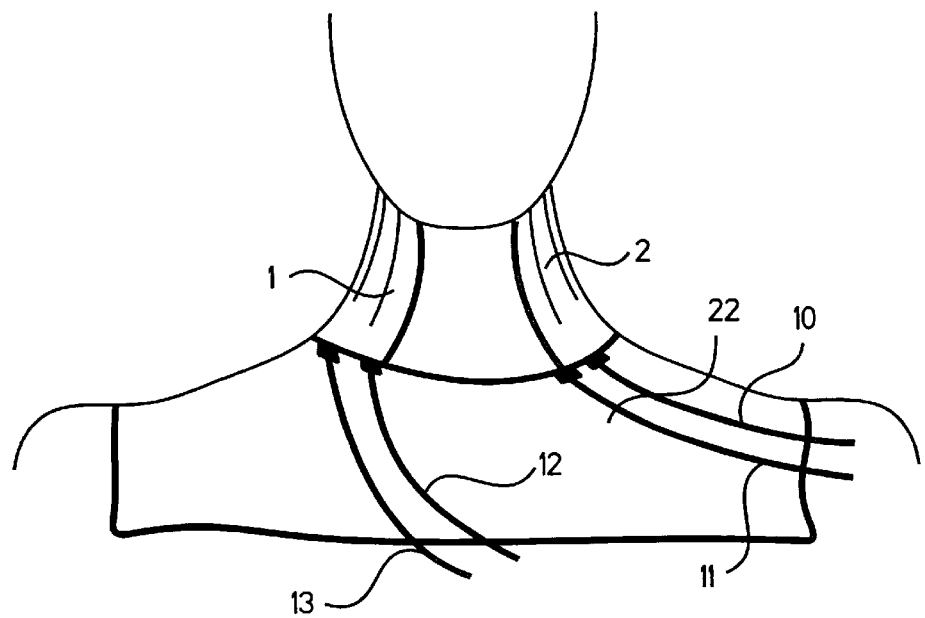
FIG. 3 is a view showing a further embodiment of the present invention.

As can be seen for example from FIG. 2, the inner surface of each pad 1, 2 can be provided with an adhesive structure, for example an adhesive layer operating on chemical principle, a mechanical principle, etc. For example a ZOLL type structure can be utilized.

FIG. 2 shows a further feature of the present invention. Here an auxiliary pad 26 is provided which is applicable on a chest area of the patient immediately adjacent to the patient's neck. Portion of the lines 10, 11, 12, 13 are attached to the outer surface of the auxiliary pad 26, for example with the use of a ZOLL BRAND type pad with VELCRO BRAND attachments, or other means. The end of the hoses which are connected to the pads 1 and 2 carry quick connectors which can be formed for example as plugs. Therefore, when necessary, the remaining portions of the apparatus can be disconnected from the pad by releasing the connections of the hoses to the pads and removing the auxiliary pad 26 which carries the end part of the hoses.

The apparatus can have 2 separate control elements, such as buttons 28, 29. By actuating one of the buttons or both buttons, one of the pumps 14, 15 or both pumps ran be turned on for circulating the cooling liquid through a corresponding one of the pads, or both pads. Of course, a multi-position switch can be also used, for these purposes. Finally, the apparatus has an on/off switch 30.

The inventive method is performed in the following manner.

The pads 1, 2 are applied to the patient's neck in the areas pad of the cartoid arteries. Cooling water is circulated through a corresponding one or both pads to cool blood in the carotid arteries and thereby to cool the brain. The temperature of the liquid is initially adjusted 1–2° C. until the monitoring indicates that the brain temperature has dropped to 34–35° C. The water temperature is then gradually elevated to maintain the brain temperature at 34–35° C., with the above described monitoring system.

It will be understood that each of the elements described above, or two or more together, may also find a useful application in other types of methods differing from the types described above.

While the invention has been illustrated and described as embodied in apparatus for and method of cooling a brain, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A method of cooling a patient's brain, comprising the steps of applying each of two hollow pads exclusively to an area of a patient's neck adjoining one of the carotid arteries so that when applied said hollow pads contact the areas exclusively adjacent to the carotid arteries and are spaced from one another; and supplying by liquid circulating means a cooling liquid from a cooling liquid source to a respective one of said pads and withdrawing liquid from the same pad, whereby the cooling liquid can circulate either through one of said pads independently from the other of said pads, or the cooling liquid can circulate through the other of said pads independently from one of said pads, or the cooling liquid can circulate through both said pads, to cool either one half of the brain, or another half of the brain, or both halves thereof.

2. A method as defined in claim 1; and further comprising adjusting a temperature of the cooling liquid in said cooling liquid source.

3. A method as defined in claim 1; and further comprising monitoring a temperature of the patient's brain, and adjusting correspondingly the temperature of the cooling liquid.

4. A method as defined in claim 3, wherein said monitoring includes monitoring by two sensors each attached to a respective half of a patient's head and each connected to said adjusting means.

5. A method as defined in claim 1; and further comprising monitoring a temperature of liquid which is supplied to a respective one of said pads, and adjusting correspondingly the temperature of the cooling liquid.

6. A method as defined in claim 5; and further comprising monitoring a temperature of liquid withdrawn from a respective one of said pads, and adjusting correspondingly the temperature of the cooling liquid.

* * * * *